United States Patent [19]

Rhyne, Jr.

[11] Patent Number: 4,659,676

[45] Date of Patent: Apr. 21, 1987

[54] FLUORESCENT TRACERS FOR HYDROPHOBIC FLUIDS

[76] Inventor: Richard H. Rhyne, Jr., 1702-B Cinnamon Path, Austin, Tex. 78704

[21] Appl. No.: 724,369

[22] Filed: Apr. 17, 1985

[51] Int. Cl.[4] ..................... G01N 33/28; G01N 21/64
[52] U.S. Cl. ........................................ 436/56; 436/27; 436/30; 436/60; 436/172; 436/178
[58] Field of Search ...................... 436/26, 27, 30, 56, 436/57, 60, 172, 178

[56] References Cited

U.S. PATENT DOCUMENTS

| | | | |
|---|---|---|---|
| 2,392,620 | 1/1946 | Sparks | 436/56 |
| 2,723,228 | 11/1955 | Moore et al. | 436/30 |
| 3,407,042 | 10/1968 | Slentz | 436/30 |
| 3,574,550 | 4/1971 | Scott et al. | 436/57 |
| 4,090,877 | 5/1978 | Streeper | 430/337 |
| 4,104,466 | 8/1978 | Tsuchida et al. | 546/2 |
| 4,213,762 | 7/1980 | Whitfill | 436/30 |
| 4,264,329 | 4/1981 | Beckett | 436/27 |
| 4,325,433 | 4/1982 | Yen et al. | 166/274 |
| 4,501,324 | 2/1985 | Sandiford et al. | 436/27 |
| 4,539,180 | 9/1985 | Schwartz | 436/172 |

*Primary Examiner*—Michael S. Marcus
*Attorney, Agent, or Firm*—Arnold, White & Durkee

[57] ABSTRACT

A fluorescently labeled complex hydrophobic fluid produced by dissolving a porphyrin therein. The porphyrin must be substantially soluble in acidic aqueous solutions, substantially insoluble in neutral or alkaline aqueous solutions and fluoresce at a wavelength between about 600 nm and 800 nm when irradiated at a wavelength between about 350 nm and 550 nm. The fluorescently labeled complex hydrophobic fluid may be identified by observation of the above-mentioned characteristic fluorescence upon irradiation. For identification purposes the porphyrin may be first extracted into an acidic aqueous solution for determination of fluorescence. In cases where the labeled hydrophobic fluid has been dispersed in a quantity of neutral or alkaline aqueous solution or suspension, this latter solution or suspension is first extracted with a hydrophobic solvent for the porphyrin to form a porphyrin solution. The prophyrin, in turn is extracted from this prophyrin solution with an acidic aqueous solution. The characteristic fluorescence of the porphyrin in the acidic aqueous solution is then determined. The concentration of the porphyrin and thus the amount of labeled hydrophobic fluid in the quantity of neutral or alkaline aqueous solution or suspension is then calculated, knowing the relationship between fluorescence and porphyrin concentration.

13 Claims, No Drawings

FLUORESCENT TRACERS FOR HYDROPHOBIC FLUIDS

BACKGROUND OF THE INVENTION

The present invention relates generally to the use and production of hydrophobic fluids comprising chemical compounds having a characteristic fluorescence. More particularly these compounds are preferably porphyrins.

In the petroleum industry there are many needs for readily identifiable hydrophobic fluids. These needs, for example, include a means for identifying crude oil or petroleum products in efforts to discourage theft.

In the process of drilling a borehole to subterranean petroleum reservoirs, a drilling mud is circulated through the drill string and borehole to carry away the cuttings, cool the drill bit and perform a number of other important functions. This drilling mud, usually an aqueous suspension with numerous components, is essential for efficient drilling. In many cases the drilling mud being circulated requires special additives which may act as lubricants and as corrosion inhibitors, as well as having other functions. These additives are usually termed drilling mud conditioners.

Since the precise volume of circulating drilling mud is often unknown, events such as loss of circulation because of penetration into porous subterranean formations or the intrusion of subterranean water or brine may cause the circulating drilling mud to have a changed content. This changed content, particularly when an optimal level of drilling mud conditioner is advisable to maintain drilling efficiency, may result in unacceptably lowered levels of drilling mud conditioner. The present invention comprises a unique method for monitoring levels of drilling mud conditioner in circulating drilling mud.

SUMMARY OF THE INVENTION

A fluorescently labeled complex hydrophobic fluid is produced by dissolving a porphyrin therein. The porphyrin must be substantially soluble in acidic aqueous solutions, substantially insoluble in neutral or alkaline aqueous solutions and fluoresce at a wavelength between about 600 nm and 800 nm when irradiated at a wavelength between about 350 nm ahd 550 nm. The intense absorption bands and the long wavelength of emission associated with porphyrins allow for their individual detection in the presence of other fluorescing species which may be naturally found in the complex hydrophobic fluid. The fluorescently labeled complex hydrophobic fluid may be identified by observation of the above-mentioned characteristic fluorescence upon irradiation. For identification purposes the porphyrin may be first extracted into an acid aqueous solution for determination of fluorescence. In cases where the labeled hydrophobic fluid has been dispersed in a quantity of neutral or alkaline aqueous solution or suspension, this latter solution or suspension is first extracted with a hydrophobic solvent for the porphyrin to form a porphyrin solution. The prophyrin is in turn extracted from this porphyrin solution with an acidic aqueous solution. The characteristic fluorescence of the porphyrin in the acidic aqueous solution is then determined. The concentration of the porphyrin and thus the amount of labeled hydrophobic fluid in the quantity of neutral or alkaline aqueous solution or suspension is then calculated, knowing the relationship between fluorescence and porphyrin concentration.

DESCRIPTION OF THE PREFERRED EMBODIMENTS

Compounds useful in the practice of the present invention fall within a class of compounds termed porphyrins. The term is used herein as defining an organic compound primarily comprising carbon, hyydrogen and nitrogen atoms, although other atoms such as oxygen, sulfur, halides or various metals, for example, may be included insofar as they or the functional groups of which they are a part, do not alter the critical solubility and fluorescence characteristics of the porphyrins described herein.

The porphyrins of the present invention comprise four pyrrole rings interconnected by four bridging meso-linkages which may be —CR= or —N= or combinations of these, where R may be an alkyl, aryl, aralkyl, alkenyl, alkenylaryl, alkenylalkyl, alkylcarboxyamide, alkylaminoalkyl, alkylcarboxyester, hydrogen or alkylalkoxy and where more than one —CR= bridging meso linkage is in a porphyrin, the R function may be independently selected for each bridging linkage. In certain cases polar R groups such as alkyl alcohol substituents, for example, may be used for form a minority of the R groups, at least insofar as the critical porphyrin solubility and fluorescence characteristics are not obviated. Such minority substitution is deemed to produce an equivalent of the porphyrins presently described.

The pyrrole rings of the porphyrins utilized in the present invention may also carry substituents in the 3 and 4 numbered carbons of each pyrrole ring (the nitrogen being position 1 and the bridging meso-linkages being connected to the 2 and 5 carbons of the pyrrole ring. The substituents in positions 3 and 4 of the porphyrin pyrrole rings may be independently selected from the same group of R substituents as in the —CR= bridging function.

In certain cases the pyrrole ring may contain a phenyl ring fused to the 3 and 4 pyrrole carbon atoms. In this situation when the meso bridging linkages are —N=, the class of porphyrins called phthalocyanines would result, many of which have the solubility and fluorescent characteristics allowing them to be used as fluorescent labels in the process of the present invention.

Terms utilized in the present description include the following.

Substantially soluble, as used herein is defined as being soluble in a particular solvent to the extent that a solution may be formed comprising at least about 0.1% by weight of the substance in question.

Substantially insoluble as used herein, is defined as being unable to dissol,ve in a particular solvent to form a solution comprising at least about 0.1% by weight of the substance in question.

Acidic aqueous solution, as used herein, is defined as a solution comprisng at least about 30 percent water and having a pH lower than about pH4.

Neutral or alkaline aqueous solution as used herein is defined as being primarily water and as having a pH greater than about pH6.

The term "extraction" as used herein, is a manipulation resulting in the transfer of a substance from one solution or suspension to another solution.

The term "drilling mud" as used herein includes water-base drilling muds (fluids). These water-base muds may include those comprising clay such as bentonite or attapulgite, barite, synthetic polymers, drill solids, potassium chloride, soda ash, caustic, lignosulfonates, lime, lignite, sea salt and/or a number of other additives. These drilling muds characteristically are thixotropic and have a specific gravity between 1.0 and 2.5.

The term "drilling mud conditioner" as used herein is defined as a hydrophobic fluid dispersible in drilling mud and usually comprising at least one of the following: a lubricant, metal corrosion control agent or shale sealing agent.

The term "hydrophobic fluid" as used herein is defined as a fluid antagonistic to water and substantially insoluble in water.

The term "complex hydrophobic fluid" as used herein, is defined as a mixture of hydrophobic liquids or a naturally occurring substance such as a crude oil.

The term "hydrophobic solvent" as used herein, is defined as a hydrophobic liquid organic compound, a mixture of such compounds or a mixture primarily comprising a hydrophobic organic compound but also containing a minor proportion of mildly hydrophobic or somewhat hydrophilic organic compound such as an alkyl alcohol or ketone.

In one aspect the present invention provides a method for determining the level of hydrophobic fluid drilling mud conditioner in water-base drilling mud during circulation through a borehole being drilled. Initially a hydrophobic fluid drilling mud conditioner is provided which comprises a dissolved porphyrin. The porphyrin, of course soluble in the hydrophobic fluid, is additionally substantially soluble in acidic aqueous solutions and substantially insoluble in neutral or alkaline aqueous solutions. In addition, the porphyrin fluoresces at a wavelength between about 600 nm and 800 nm when irradiated at a wavelength between about 350 nm and 550 nm.

The hydrophobic fluid drilling mud conditioner comprising said dissolved porphyrin is mixed into the drilling mud to produce a conditioned mud which is then circulated downhole, usually pumped down through a hollow drill pipe to the bit and returned from the bottom of the hole to the surface through the annular space ouside the drill pipe.

When desired, a sample of the circulating conditioned drilling mud is obtained, taken for example, from beneath the shale shaker. The porphyrin in this sample of circulated conditioned drilling mud is then extracted with an amount of hydrophobic solvent for said porphyrin to produce a porphyrin solution. The porphyrin is then re-extracted from an amount of the porphyrin solution into an acidic aqueous solvent to produce an acidic aqueous solution or porphyrin.

The acidic aqueous solution of porphyrin is then irradiated at a wavelength between about 350 nm and 550 nm and resultant fluorescence at a wavelength between about 600 nm and 800 nm is measured. From the measurement of fluorescence, the level of drilling mud conditioner in the circulated conditioned drilling mud is determined. The drilling operator or mud engineer may then decide as to whether the addition of further drilling mud conditioner to the circulating drilling mud is desired.

A fluorescently labeled hydrophobic fluid drilling mud conditioner may be produced as described in this process. The address of dissolved porphyrin, as described above, provides a method for producing identifiable complex hydrophobic fluids such as crude oils.

The preferred concentration range of porphyrins in hydrophobic fluids for any of the above described purposes is between about 0.05 gm per gallon and about 1.0 gm per gallon.

A preferred method of adding porphyrin to a hydrophobic fluid is by first preparing a concentrated or saturated methylene chloride solution of the porhyrin and then adding a predetermined amount of the saturated solution to the hydrophobic fluid. Methylene chloride, if desired, may be removed from the porphyrin labeled hydrophobic fluid by raising its temperature to above about 50 degrees centigrade.

Specific porphyrins usable in the practice of the present invention include: meso-tetraphenylporphyrin (SAR Chemical, Inc.) which has a phenyl group as R attached to each meso bridging function —CR=; octaethyl porphine (Aldrich Chemical Co.) which has an ethyl group at the 3 and 4 carbons of each pyrrole ring; and protoporphyrin IX dimethyl ester (Aldrich Chemical Co.) which has pyrrole substituents at positions 3 and 4 of methyl, vinyl and esterified alkyl carboxy functional groups.

In a series of experiments, a drilling mud conditioned with meso-tetraphenyl porphyrin labeled conditioner was incubated in a metal pipe bomb at 400 degrees Fahrenheit for up to several hours. This heating had no deleterious effects on the amount of extractable meso-tetraphenyl porphyrin and its fluorescence properties.

The following examples are presented to illustrate embodiments of the present invention and are not meant to limit the scope of the present invention unless specifically included in appended claims.

EXAMPLE 1

On June 15, 1984, a well owned by Exxon Corp. (Overton GU8 #2) was being drilled in Smith County, Texas by Rainbow Drilling and was to a depth of 8539 ft. A labeled hydrophobic fluid drilling mud conditioner (Triple SSS ®, Tech Oil, Inc.) was prepared by adding ⅛ gm meso-tetraphenylporphyrin per gallon conditioner and mixing thorougly at about 140° F. Two hundred eighty gallons of the labeled mud conditioner was added to the 1,000 barrel water-base drilling mud system to formulate a conditioned drilling mud having about 2 lb conditioner per barrel.

A 2 lb per barrel standard was prepared by mixing 2.33 ml of the labeled conditioner with 350 ml drilling mud and mixing for 5 minutes with a 1/15 hp high speed mixer (OFI Testing Equipment Co.).

The conditioned mud was circulated through the well bore and mud samples were periodically taken from beneath the shale shaker. Both the drilling mud standard and the samples of circulated mud were subjected to the following measurement and manipulations.

Thirty ml of mud was placed in a 125 ml polypropylene bottle. Forty ml of cyclohexane was added to the mud and the bottle was shaken by hand for 30 seconds. Subsequently, 5 ml of ethanol was added to the mud-cyclohexane mixture which was again shaken for 30 seconds. Such ethanol addition had been found to increase extraction efficiency by about 10% although the causative mechanism and distribution of ethanol is unknown. To separate the mud from the hydrophobic solvent, successive ¼ tsp amounts of flocculant (Imco Floc, IMCO Services) were added to the mud-solvent mixture, followed by repeated shakings. When a solvent phase separated from the mud-flocculant composit, flocculant addition was stopped and a 4 ml sample of the porphyrin solution in cyclohexane and ethanol was withdrawn.

Each 4 ml sample of porphyrin solution was placed in a 3 dram screw-cap vial and mixed with 4 ml of an acidic aqueous solution of concentrated hydrochloric acid:isopropanol:water, 1:1:1. Each vial was vigorously shaken for one minute and the aqueous and hydrophobic fluid phases allowed to separate. The one-minute shaking period should be the same for each sample and standard. This shaking time is recommended for maximal extraction efficiency and lesser differences in extraction beween samples shaken for slightly different times.

Each separated acidic aqueous solution phase was withdrawn with a 5 ml syringe and filtered through a 0.45 micron syringe filter assembly to remove any particulate matter. The filtered solution was then placed in a 4-sided plastic cuvet for excitation and measurement of fluorescence.

An SAR Chemical, Inc. model 1000 filter fluorimeter, equipped with an excitation light filter system of a Corning 5-60 filter in conjunction with a blue T-5 envelope lamp, was used to irradiate the sample in the cuvet with light having a peak wavelength of about 440 nm. Fluorescent light have a wavelength of about 690 nm and emitted from a transverse side of the cuvet was passed through a Corning 2-58 sharp cut filter and was detected by a Hamamatsu S1226-8BK silicon photocell and read as an electrical signal on a panel voltmeter. When the porphyrin acidic aqueous extract derived from the drilling mud 2 lb per barrel standard was measured for fluorescence in the system described above, the gain control was adjusted so that, for convenience, a voltmeter reading of "4" was obtained. The gain control was then not adjusted for subsequent samples of porphyrin extracted from circulated conditioned drilling mud.

Several samples of conditioned mud taken after about one circulation through the borehole produced fluorescence signals on the voltmeter within 10% of a "4" reading. Conditioned drilling mud samples taken after about 12 hours of circulation resulted in a voltmeter reading of about "3" which indicated a 25% decline in the fluorescent meso-tetraphenylporphyrin and thus a drilling mud conditioner level of about 1.5 lb per barrel. Further labeled Triple SSS mud conditioner was then added to the circulating mud until circulated mud samples gave a fluorescence reading of "4" again.

During the next 24 days of drilling, the level of labeled drilling mud conditioner was determined regularly and repeatedly shown to decrease by about ¼ to ½ lb per barrel during twelve hours of circulation.

During particularly difficult periods of drilling requiring higher levels of conditioner, the labeled Triple SSS was raised to 3 lb per barrel and a fresh standard of the same drilling mud with this level of conditioner was prepared. The analogous instrument standardization, extraction procedures and monitoring gave similar results.

EXAMPLE 2

Meso-tetraphenylporphyrin in Mineral Oil Conditioner

Meso-tetraphenylporphyrin (1.2 mg) was dissolved in 0.4 ml methylene chloride and added to 12 gm mineral oil (Whitco Chemical, 210 USP). The resultant solution (or labeled drilling mud conditioner model) was heated briefly to about 60 degrees centigrade to remove methylene chloride. Various amounts of this labeled mineral oil were added to a 14 lb/gal lignosulfonate drilling mud and thoroughly mixed to produce conditioned drilling mud with labeled conditioner at ½ lb per barrel, 1 lb per barrel and 2 lb per barrel.

The extraction procedure described in Example 1 was followed for each of these muds, as well as for a mud without any labeled conditioner, to result in acidic aqueous extractions to be subjected to fluorescence measurements.

A Spex Industries Model No. 1902 fluorolog spectrometer was used for fluorescence measurements. This instrument had a 150 W xenon light source, double monochromators on both the excitation light path and the emission light path, and an RCA C31034 photomultiplier operated in the photon counting mode and held in a Pacific Precision Model No. 3470 cooled housing at minus 30 degrees centigrade. Emission and excitation slit widths were set for a 10 nm band pass and a standard glass 4-sided cuvet was used to hold the sample. With an excitation light wavelength of 440 nm, fluorescence emission was monitored at a wavelength of 693 nm. The fluorescence signals obtained from these manipulations are shown in Table 1.

TABLE 1

| Labeled Conditioner lb/barrel mud | Fluorescence Signal |
| --- | --- |
| 0 | 0.0 |
| ½ | 0.8 |
| 1 | 1.6 |
| 2 | 3.0 |

These results demonstrate the usability of meso-tetraphenylporphyrin as a drilling mud conditioner label when the drilling mud conditioner is of a wholly known composition. The approximately linear relationship between fluorescence signal and labeled conditioner content is again extant.

EXAMPLE 3

Octaethylporphine Label

The procedure described in Example 2 was followed with the following modifications. One mg octaethylporphine (Aldrich Chemical Co.) was dissolved in 10 g Triple SSS mud conditioner and the acidic aqueous extract was excited at a wavelength of 405 nm and fluorescence monitored at 656 nm. The results are shown in Table 2.

TABLE 2

| Labeled Conditioner lb/barrel mud | Fluorescence Signal |
| --- | --- |
| 0 | 0.0 |
| 1 | 0.6 |
| 2 | 1.1 |

Analogously, the utility of another porphyrin, octaethylporphine, is demonstrated.

EXAMPLE 4

Protoporphyrin IX, Dimethyl Ester Label

The procedure described in Example 2 was followed with the following modifications. One mg of protoporphyrin IX, dimethyl ester was dissolved in 10 g Triple SSS mud conditioner. Excitation was at 414 nm and fluorescence was monitored at 667 nm. The results are shown in Table 3.

TABLE 3

| Labeled Conditioner lb/barrel mud | Fluorescence Signal |
| --- | --- |
| 0 | 0.0 |
| 1 | 0.3 |
| 2 | 0.5 |

The approximately linear relationship between fluorescence signal and labeled conditioner level demonstrates the utility of this porphyrin.

EXAMPLE 5

Other Porphyrins

Both hematoporphyrin IX containing polar alkyl carboxy and alkyl alcohol pyrrole side chains and protoporphyrin IX disodium salt, with two vinyl pyrrole side chains, four methyl pyrrole side chains and two alkylcarboxy side chains failed to properly function in runs analogous to those of Examples 2, 3 or 4. This failure was ascribed to the polarity or hydrophilicity of the pyrrole substituents which rendered these derivatives insoluble in the hydrophobic fluid conditoner and also more soluble in the alkaline aqueous solution comprised in the lignosulfonate drilling mud.

Changes may be made in the construction, operation and arrangement of the various parts, elements, steps and procedures described herein without departing from the concept and scope of the invention as defined in the following claims.

What is claimed is:

1. A method of determining the level of hydrophobic fluid drilling mud conditioner contained in water-base drilling mud circulated through a borehole being drilled comprising the steps of:

providing a hydrophobic fluid drilling mud conditioner comprising a dissolved porphyrin, said porphyrin being substantially soluble in acidic aqueous solutions, substantially insoluble in neutral or alkaline aqueous solutions and fluorescing at a wavelength between about 600 nm and 800 nm when irradiated at a wavelength between about 350 nm and 550 nm;

mixing said hydrophobic fluid drilling mud conditioner into the drilling mud to produce a conditioned mud;

circulating the conditioned mud through the borehole;

extracting a sample of circulated conditioned mud with an amount of a hydrophobic solvent for said porphyrin, to produce a porphyrin solution;

reextracting the porphyrin from an amount of the porphyrin solution into an acidic aqueous solvent to produce an acidic aqueous solution of porphyrin;

irradiating the acidic aqueous solution of porphyrin at a wavelength between about 350 nm and about 550 nm and measuring fluorescence at a wavelength between about 600 nm and about 800 nm; and determining, from the fluorescence measured, the level of drilling mud conditioner in the circulated conditioned drilling mud.

2. The method of claim 1, wherein the porphyrin is dissolved in an amount between about 0.05 gm per gallon and 1.0 gm per gallon.

3. The method of claim 1, wherein the porphyrin is meso-tetraphenylporphyrin.

4. The method of claim 1, wherein the porphyrin is octaethyl porphine.

5. The method of claim 1, wherein the porphyrin is protoporphyrin IX dimethyl ester.

6. The method of claim 1, wherein the porphyrin is a phthalocyanine.

7. The method of claim 1, wherein the porphyrin is irradiated at a wavelength of about 440 nm and fluoresces at a wavelength of about 690 nm.

8. The method of claim 1 wherein the hydrophobic fluid drilling mud conditioner comprises a mineral oil.

9. The method of claim 1, wherein:

the porphyrin compound is meso-tetraphenylporphyrin in a concentration of about $\frac{1}{2}$ gm per gallon; and the conditioned mud contains about 2 pound drilling mud conditioner per barrel.

10. The method of claim 1 wherein the extracting step is defined further: the sample being about 30 ml; the hydrophobic solvent being cyclohexane in an amount of about 40 ml and comprising about 10% ethanol; and a flocculant is added in an amount sufficient to coagulate mud particles and allow an hydrophobic porphyrin solution to separate after vigorous shaking and settlement.

11. The method of claim 1 wherein the acidic aqueous solvent is concentrated HCl:isopropanol:water in a 1:1:1 ratio and the acidic aqueous solvent is in an amount about the same as the amount of porphyrin solution.

12. The method of claim 1, where the porphyrin is first dissolved in methylene chloride to form a solution and the solution is added to the hydrophobic fluid.

13. The method of claim 1, wherein the porphyrin comprises four pyrrole rings interconnected by meso bridging functions —CR= between the 2 and 5 positions of each pyrrole ring and the pyrrole ring further has R substituents at the 3 and 4 positions where each R is independently from the group consisting of alkyl, aryl, aralkyl, alkenyl alkenylaryl, alkenylalkyl, alkylcarboxyamide, alkylcarboxyester, alkylaminoalkyl, alkylalkoxy and hydrogen.

* * * * *

UNITED STATES PATENT AND TRADEMARK OFFICE
CERTIFICATE OF CORRECTION

PATENT NO. :  4,659,676
DATED     :  April 21, 1987
INVENTOR(S) :  Richard H. Rhyne, Jr.

It is certified that error appears in the above-identified patent and that said Letters Patent is hereby corrected as shown below:

Column 1, line 47, delete the word
    "ahd" and insert therefor the word --and--.

Column 2, line 54, delete the word
    "dissol,ve" and insert therefor the word --dissolve--.

Column 2, line 58, delete the word
    "comprisng" and insert therefor the word --comprising--.

Column 3, line 44, delete the word
    "ouside" and insert therefor the word --outside--.

Column 3, line 66, delete the word
    "address" and insert therefor the word --addition--.

Column 4, line 41, delete the word
    "thorougly" and insert therefor the word --thoroughly--.

UNITED STATES PATENT AND TRADEMARK OFFICE
CERTIFICATE OF CORRECTION

PATENT NO. : 4,659,676

DATED : April 21, 1987

INVENTOR(S) : Richard H. Rhyne, Jr.

It is certified that error appears in the above-identified patent and that said Letters Patent is hereby corrected as shown below:

Column 4, line 43, delete the number
"1,000" and insert therefor the number --1,100--.

Column 4, line 54, delete the word
"measurement" and insert therefor the word --measurements--.

Column 5, line 46, insert the symbol
--•-- between the letters "SSS" and the word "mud".

Column 5, line 55, insert the symbol
--•-- between the letters "SSS" and the word "was".

Column 6, line 66, insert the symbol
--•-- between the letters "SSS" and the word "mud".

Claim 9, column 8, line 29, delete the word
"pound" and insert therefor the word --pounds--.

Signed and Sealed this

Twenty-fourth Day of November, 1987

Attest:

DONALD J. QUIGG

Attesting Officer

Commissioner of Patents and Trademarks